United States Patent [19]
Mackman et al.

[11] Patent Number: 5,866,702
[45] Date of Patent: *Feb. 2, 1999

[54] PURINE INHIBITORS OF CYCLIN DEPENDENT KINASE 2

[75] Inventors: Richard Mackman, San Carlos; Robert T. Lum, Palo Alto; Steven R. Schow, Redwood City, all of Calif.; Michael M. Wick, Chestnut Hill, Mass.

[73] Assignee: CV Therapeutics, Incorporation, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 692,012

[22] Filed: Aug. 2, 1996

[51] Int. Cl.$^6$ .................. A61K 31/52; C07D 473/16; C07D 473/40; C07D 473/18
[52] U.S. Cl. .................. 544/277; 544/276; 544/268; 544/269; 544/118
[58] Field of Search .................. 544/276, 277; 514/261, 262, 265, 266, 263

[56] References Cited

U.S. PATENT DOCUMENTS

| | | | |
|---|---|---|---|
| 4,028,353 | 6/1977 | Liotta, et al. | 544/277 |
| 4,405,781 | 9/1983 | Bader et al. | 544/264 |
| 5,498,819 | 3/1996 | Kaneko et al. | 544/277 |
| 5,508,277 | 4/1996 | Regnier et al. | 544/264 |

FOREIGN PATENT DOCUMENTS

| | | | |
|---|---|---|---|
| WO 93/17020 | 9/1993 | WIPO | 544/277 |
| WO 93/17020 A1 | 9/1993 | WIPO . | |
| WO 97/16452 | 5/1997 | WIPO . | |
| WO 97/18212 | 5/1997 | WIPO . | |
| WO 97/20842 | 6/1997 | WIPO . | |

OTHER PUBLICATIONS

Glab et al., FEBS Letters 353, pp. 207–211, Olomoucine, an inhibitor of the cdc2/cdk2 kinases activity, blocks plant cells at the G1 to S and G2 to M cell cycle transitions (1994).
Abraham et al., Biol Cell 83, pp. 105–120, Cellular effects of olomoucine, an inhibitor of cyclin–dependent kinases (1995).
Schulze–Gahmen et al., Proteins: Structure, Function, and Genetics 22, pp. 378–391, Multiple Modes of Ligand Recognition: Crystal Structures of Cyclin–Dependent Protein Kinase 2 in Complex with ATP and Two Inhibitors, Olomoucine and Isopentenyladenine (1995).
Vesely et al., Eur. J. Biochem. 224, pp. 771–786, Inhibition of cyclin–dependent kinases by purine analogues (1994).
Norman et al., J. Am. Chem. Soc. 118, pp. 7430–7431, A Structure–Based Library Approach to Kinase Inhibitors (1996).

Breshears, et al. Journal of the American Chemical Society, vol. 81, pp. 3789–3792, The Aminolysis of Certain Chlorosubstituted Purines (1959).
Breshears, J. A. C. S 81, 3789 (1959).

Primary Examiner—Mark L. Berch
Attorney, Agent, or Firm—Mcdonnell, Boehnen Hulbert & Berghoff

[57] ABSTRACT

A 2,6,9-trisubstituted purine composition having the following formula:

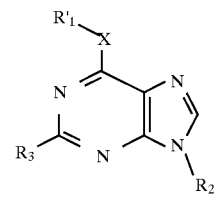

where X is a amino, oxo, thio, of sulfone moiety, $R_1$ is a lower alkyl, substituted lower alkyl, cycloalkyl, substituted cycloalkyl, cycloheteroalkyl, substituted cycloheteroalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl, each having from 1 to 20 carbon atoms; $R_2$ is hydrogen, lower alkyl, substituted lower alkyl, cycloalkyl, substituted cycloalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl; and $R_3$ is halogen, hydroxyl, thio, alkoxy, alkylthio, lower alkyl, —$NR_4R_5$ or a component having the formula:

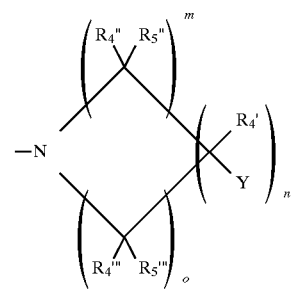

wherein when $R_3$ is 2-hydroxyethylamino and $R_2$ is methyl, $R_1$-X is not amino, 3-methyl-2-butenylamino, benzylamino, or m-hydroxybenzyl-amino, when $R_3$ is 2-hydroxyethylamino and $R_2$ is isopropyl, $R_1$-X is not benzylamino, m-hydroxybenzylamino, or 3-methylbutylamino, when $R_3$ is 2-hydroxyethylamino and $R_2$ is 2-hydroxyethyl, $R_1$-X is not benzylamino and when $R_3$ is selected from the group consisting of 2-propanol-2-methylamino and 2-dimethylaminoethylamino and $R_2$ is methyl, then $R_1$-X is not benzylamino.

6 Claims, 1 Drawing Sheet

PURINE INHIBITORS OF CYCLIN DEPENDENT KINASE 2

BACKGROUND OF THE INVENTION

(1.) Field of the Invention

This invention concerns 2,6,9-trisubstituted purines that have been discovered to be selective inhibitors of cell cycle kinases and, as such, the compounds are inhibitors of cell proliferation. The 2,6,9-trisubstituted purines are useful in for example in—treating autoimmune diseases, e.g. rheumatoid arthritis, lupus, type I diabetes, multiple sclerosis, etc., in treating cancer, cardiovascular disease, such as restenosis, host vs graft disease, gout, polycystic kidney disease and other proliferative diseases whose pathogenesis involves abnormal cell proliferation.

(2.) Description of the Art

In the past few years, advances in molecular and cellular biology have contributed to our understanding of the mechanisms of cell proliferation and of specific events that occur during progression of cells through mitosis. E.g., "Progress in Cell Cycle Research" Vol 1, Eds. L. Meijer, S. Guidet and H. Y. L. Tung; Plenum Press, New York, 1995. These studies have shown that progression through the cell cycle is controlled by a family of serine/threonine kinases called cyclin dependent kinases. These enzymes contain (a) a catalytic protein called cyclin dependent kinase (CDK) that uses ATP as a substrate and (b) a regulatory protein called cyclin. Different cyclin-CDK combinations control events such as growth, DNA replication and cell division. One key member of the CDK family of enzymes is CDK2. CDK2 activity has been shown to be essential for mammalian cell cycle progression at the G1/S boundary. Microinjection of antibodies directed against CDK2 blocks the progression of human diploid fibroblasts into the S phase of the cell cycle. Expression of a CDK2 dominant negative mutant in human osteosarcoma cells has a similar effect. Together, these studies indicate that inhibition of cellular CDK2 activity will prevent progression of cells through the mitotic cycle and induce growth arrest prior to the S phase. Consistent with this view, in vitro studies with olomoucine (2-(hydroxyethylamino)-6-benzylamino-9-methylpurine), have shown that it is a specific inhibitor of CDK2 with an $IC_{50}$ of approximately 2.1 µg/ml J. Vesely, et al.; Eur. J.Biochem 224, 771–786 (1994), L. Meijer "Chemical Inhibitors of Cyclin-Dependent Kinases" pp 351–356 in "Progress in Cell Cycle Research Vol 1, Eds. L. Meijer, S. Guidet and H. Y. L. Tung; Plenum Press, New York, 1995. In vivo studies using mammalian cells in culture have shown that olomoucine inhibits cell proliferation at an approximate concentration of 50 µg/ml.

In this invention, we have developed several compounds whose biological activity is considerably more potent than olomoucine. In vivo studies using mammalian cells indicate that some of the disclosed compounds inhibit cell proliferation at concentrations that are significantly lower than olomoucine.

SUMMARY OF THE INVENTION

It is an object of this invention to provide 2,6,9-trisubstituted purine compounds, which inhibit the cyclin dependent kinase 2.

It is another object of this invention to provide 2,6,9-trisubstituted purine compounds which are useful for inhibiting cell proliferation.

This invention also constitutes a pharmaceutical composition, which comprises a 2,6,9-trisubstituted purine compound and a pharmaceutically acceptable carrier.

This invention further constitutes a method for inhibiting cell proliferation, which comprises administering to a mammal in need thereof an effective amount of a 2,6,9-trisubstituted purine compound.

In one embodiment, this invention is A 2,6,9-trisubstituted purine composition of matter having the following formula:

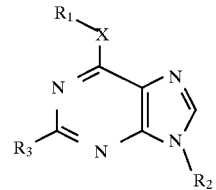

where X is a NH, O, thio, or sulfone moiety;

$R_1$ is a lower alkyl, substituted lower alkyl, cycloalkyl, substituted cycloalkyl, cycloheteroalkyl, substituted cycloheteroalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl, each having from 1 to 20 carbon atoms;

$R_2$ is lower alkyl, substituted lower alkyl, cycloalkyl, substituted cycloalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl;

$R_3$ is halogen, hydroxyl, thio, alkoxy, alkylthio, lower alkyl, —$NR_4R_5$ or a component having the formula:

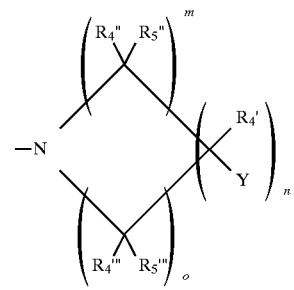

where m=1–3, n=1–3, and o=1–3; Y=carbonyl, —$NR_4R_5$, hydroxyl, thiol, alkoxy, alkythio, and wherein $R_4$ and $R_5$ are each independently selected from the group including hydrogen, lower alkyl, substituted lower alkyl, alkoxy, amino, amido, carboxyl, cycloalkyl, substituted cycloalkyl, heterocycle, cycloheteroalkyl, substituted cycloheteroalkyl, acyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, or cyano; wherein Y and $R_4'$ together may be a single oxygen atom in the composition, $R_4''$ and $R_5''$ may be a single oxygen atom and $R_4'''$ and $R_5'''$ may be a single oxygen atom and wherein when $R_3$ is 2-hydroxyethylamino and $R_2$ is methyl, $R_1$-X is not 3-methyl-2-butenylamino, benzylamino, or m-hydroxybenzyl-amino, when $R_3$ is 2-hydroxyethylamino and $R_2$ is isopropyl, $R_1$-X is not benzylamino, m-hydroxybenzylamino, or 3-methylbutylamino, when $R_3$ is 2-hydroxyethylamino and $R_2$ is 2-hydroxyethyl, $R_1$-X is not benzylamino and when $R_3$ is selected from the group consisting of 2-methyl-2hydroxy propylamino and 2-dimethylaminoethylamino and $R_2$ is methyl, then $R_1$-X is not benzylamino.

In another embodiment, this invention is a method for inhibiting cell proliferation in mammals comprising administering a therapeutically effective amount of the composition of claim 1 to the mammal. The method is useful for treating cell proliferation disorders such at rheumatoid artritis, lupus, type I diabetes, multiple sclerosis, cancer, restenosis, host graft disease, and gout.

In yet another embodiment, this invention is a pharmaceutical composition of matter comprising the composition above in an admixture with one or more pharmaceutical excipients.

In still another embodiment, this invention is a composition useful for treating fungal infections (fungi) in humans, animals, and in plants.

DESCRIPIION OF THE, CURRENT EMBODIMENT

Figure 1:
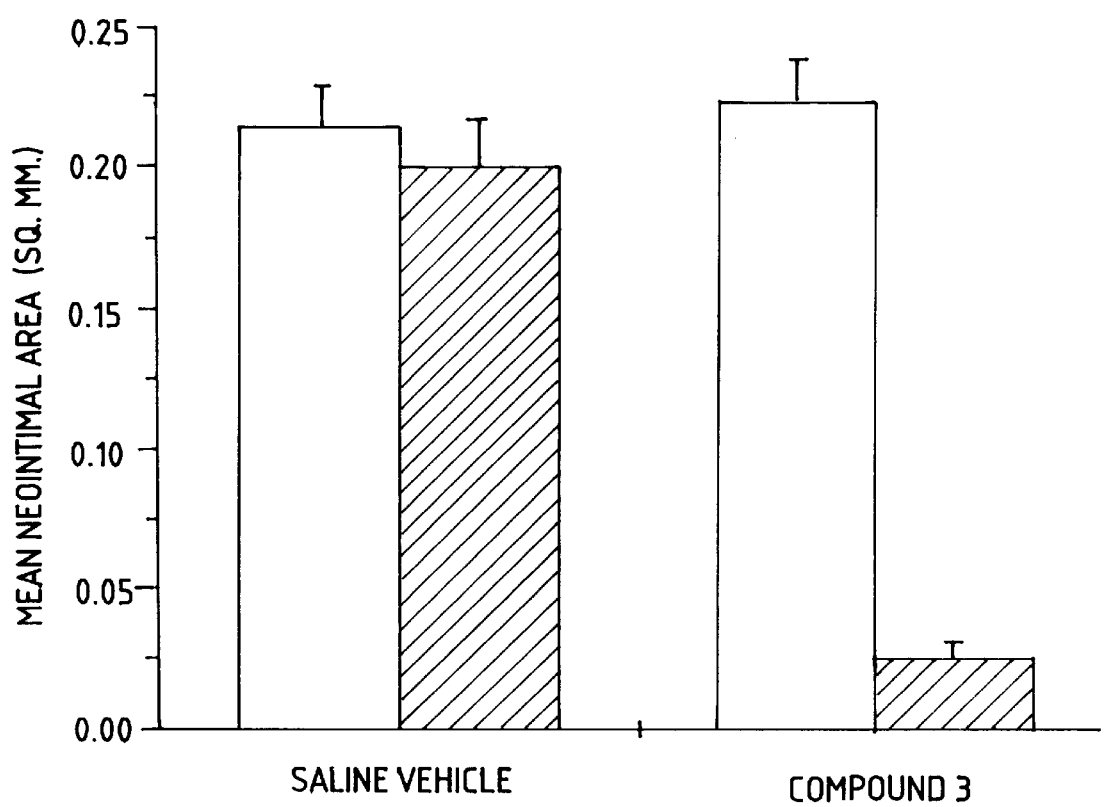
FIG. 1 is a plot of the mean neointimal area of a rat carotid artery treated with a saline vehicle and treated with compound 3 prepared according to Example 2 wherein the unshaded bar represents the untreated section of the carotid artery and the shaded bar represents the treated section of the carotid artery.

The present invention relates to a 2,6,9-trisubstituted purine compound having the following formula:

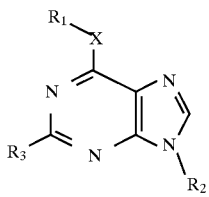

where:

X is a NH, O, thio, or sulfone moiety. X is preferably amino.

$R_1$ may be a lower alkyl, substituted lower alkyl, cycloalkyl, substituted cycloalkyl, cycloheteroalkyl, substituted cycloheteroalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl, each having from 1 to 20 carbon atoms. $R_1$ is preferably $CH_2$-aryl, $CH_2$-substituted aryl, 4-methoxybenzyl, 4-chlorobenzyl, or 4-nitro benzyl.

$R_2$ may be lower alkyl, substituted lower alkyl, cycloalkyl, substituted cycloalkyl, aryl, substituted aryl, heterocycle, hetaryl, substituted hetaryl, aralkyl, heteroaralkyl, heteroalkyl, alkyl alkenyl, alkyl alkynyl, alkyl cycloalkyl, or alkyl cycloheteroalkyl where the hydrocarbon compounds have from 1 to 20 carbon atoms. $R_2$ is preferably isopropyl.

$R_3$ is halogen, hydroxyl, thio, alkoxy, alkylthio, lower alkyl, —$NR_4R_5$ or a component having the formula:

$$-N \begin{pmatrix} R_4{''} & R_5{''} \\ & \\ R_4{'''} & R_5{'''} \end{pmatrix}_m \begin{pmatrix} R_4{'} \\ Y \end{pmatrix}_n$$

where m=1–3, n=1–3, o=1–3, Y=carbonyl, —$NR_4R_5$, hydroxyl, thiol, alkoxy, alkythio, and wherein $R_4$ and $R_5$ are each selected from the group including hydrogen, lower alkyl, substituted lower alkyl, alkoxy, amino, amido, carboxyl, cycloalkyl, substituted cycloalkyl, heterocycle, cycloheteroalkyl, substituted cycloheteroalkyl, acyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, or cyano having from 1 to 20 carbon atoms, and preferably from 2 to 6 carbon atoms. Furthermore, Y and $R_4'$ may together be a single oxygen atom in the composition, $R_4''$ and $R_5''$ may together be a single oxygen atom and $R_4'''$ and $R_5'''$ may be a single oxygen atom. $R_4$ and $R_5$ are preferably the same or different substituted lower alkyl having from 2 to 6 carbon atoms including —$CH_2CH_2OH$ and —$CH_2CH(CH_3)OH$.

There are some limitations to the scope of R, $R_1$, $R_2$ and $R_3$. When $R_3$ is 2-hydroxyethylamino and $R_2$ is methyl, $R_1$-X cannot be RNH, 3-methyl-2-butenylamino, benzylamino, or m-hydroxybenzyl-amino. When $R_3$ is 2-hydroxyethylamino and $R_2$ is isopropyl, $R_1$-X cannot be benzylamino, m-hydroxybenzylamino, or 3-methylbutylamino. When $R_3$ is 2-hydroxyethylamino and $R_2$ is 2-hydroxyethyl, $R_1$-X cannot be benzylamino. When $R_3$ is 2-methyl-2-hydroxy propylamino 2-dimethylaminoethylamino and $R_2$ is methyl, $R_1$-X cannot be benzylamino.

The following are definitions for certain terms used herein. "Halogen" refers to fluorine, bromine, chlorine, and iodine atoms. "Hydroxyl" refers to the group —OH. "Thiol" or "mercapto" refers to the group —SH.

"Lower alkyl" refers to a cyclic, branched or straight chain, alkyl group of one to ten carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, hexyl and the like.

"Substituted lower alkyl" refers to lower alkyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, cyano. These groups may be attached to any carbon atom of the lower alkyl moiety.

"Alkyl alkenyl" refers to a group —R—CR'=CR'''R'''', R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below. "Alkyl alkynyl" refers to a groups —RC≡CR' where R, lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined.

"Acyl" denotes groups —C(O)R, where R is hydrogen, lower alkyl substituted lower alkyl, aryl, substituted aryl and the like as defined below.

"Aryloxy" denotes groups —OAr, where Ar is an aryl, substituted aryl, heteroaryl, or substituted heteroaryl group as defined below.

"Amino" denotes the group NRR', where R and R' may independently by hydrogen, lower alkyl, substituted lower alkyl, aryl, substituted aryl, hetaryl, or substituted hetaryl as defined below or acyl.

"Amido" denotes the group —C(O)NRR', where R and R' may independently by hydrogen, lower alkyl, substituted lower alkyl, aryl, substituted aryl, hetaryl, substituted hetaryl as defined below.

"Carboxyl" denotes the group —C(O)OR, where R may independently be hydrogen, lower alkyl, substituted lower alkyl, aryl, substituted aryl, hetaryl, substituted hetaryl and the like as defined.

"Aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl" or "hetar" refers to a heterocycle in which at least one heterocyclic ring is aromatic.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Aralkyl" refers to the group —R-Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, hetaryl, substituted hetaryl, nitro, cyano, thiol, sulfamido and the like.

"Cycloheteroalkyl " refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optional be unsubstituted or substituted with e.g. halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optional be unsubstituted or substituted with e.g. halogen, lower alkyl, lower alkoxy, alkylthio, amino, amido, carboxyl, acetylene, hydroxyl, aryl, aryloxy, heterocycle, hetaryl, substituted hetaryl, nitro, cyano, thiol, sulfamido and the like.

If the final 2,6,9-trisubstituted purine compound of this invention contains a basic group, then an acid addition salt of the composition may be prepared. Acid addition salts of the compounds of this invention are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful.

If the final 2,6,9-trisubstituted purine compound contains an acidic group, then cationic salts of the composition may be prepared. Typically the acidic parent compound is treated with an excess of an alkaline reagent, such as hydroxide, carbonate or alkoxide, containing the appropriate cation such as Na+, K+, Ca+2 and NH4+. Certain of the compounds form inner salts or zwitterions which may also be acceptable.

The compounds of this invention are useful in inhibiting cell proliferation in mammals including humans. The 2,6, 9-trisubstituted purines are useful in for example in—treating autoimmune diseases, e.g. rheumatoid arthritis, lupus, type I diabetes, multiple sclerosis, etc., in treating cancer, cardiovascular disease, such as restenosis, host vs graft disease, gout, polycystic kidney disease and other proliferative diseases whose pathogenesis involves abnormal cell proliferation.

The method of treatment comprises the administration parenterally, and orally, of an effective quantity of the chosen compound, preferably dispersed in a pharmaceutical carrier. Therapeutically useful amounts of the composition of this invention will generally range from about 0.01 to about 100 mg/kg, but will be readily determined by one skilled in the art depending upon the route of administration, and the age and condition of the patient. Therapeutically useful amounts of the composition of this invention may be administered from one to ten times daily or more for acute or chronic disease. No unacceptable toxicological effects are expected when compounds of the invention are administered in accordance with the present invention.

The compounds of this invention are also useful as antifungal agents. As such, the compositions of this invention are useful for treating fungal infections in humans, animals, and in plants.

Pharmaceutical compositions including the compounds of this invention, and/or derivatives thereof, may be formulated as solutions or lyophilized powders for parenteral administration.

Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acaia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention. In the Examples, all temperatures are in degrees Centigrade. RT indicates room temperature.

EXAMPLE 1

The compounds of this invention are prepared by conventional methods of organic chemistry. The reaction sequence outlined in the synthesis scheme below is a general method useful for the synthesis of compounds of this invention. 2,6-dichloropurine is dissolved in butanol and the appropriate $R_1$ amine is added. After heating for several hours, the reaction mixture is cooled, and the compound 1 is obtained. To compound 1, is added, sodium hydride followed by $R_2$, and compound 2 is isolated. To compound 2, $R_3$ is added in solution with N-methylpyrrolidinone. The mixture is heated for an appropriate period followed by purification leading to the desired compound.

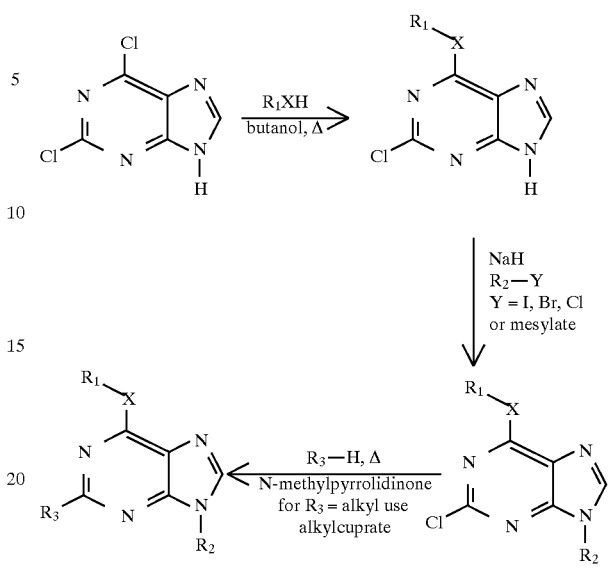

The following compound was prepared according to the method above.

2-chloro-6-(4-methoxybenzylamino) purine (1).

The 2,6-dichloropurine (4.06 g, 21.5 mmol) was suspended in butanol (150 ml) and the 4-methoxybenzylamine was added (3.4 ml, 26 mmol). The solution turned clear and then cloudy a few minutes later. The solution was heated at 120° C. for 2 hr and then cooled. The butanol was evaporated followed by suspension of the residue in water and diethyl ether mixture. A solution of 2N NaOH (1.3 ml, 26 mmol) was added and the solution stirred for 10 min before filtration. The filtered precipitate was washed with water and a small amount of ether and then dried under vacuum. The residual liquor was left overnight and more xtals were collected the next day and washed with diethyl ether. Yield =71%.

Preparation of 2-chloro-6-(4-methoxybenzylamino)-9-isopropylpurine (2) The 6-(4-methoxybenzylamino)-2-chloropurine (496 mg, 1.7 mmol) was suspended in dry DMF (5 ml) and treated with sodium hydride, 60% dispersion (82 mg, 2.06 mmol). The suspension was stirred for 30 min over which time it became a clear yellow/green solution. 2-Iodopropane (0.280 mL, 1.7 eq.) was added over 5 min and the resultant solution stirred for 2 days. Water was added and the solution and extracted with ethyl acetate. The organic layer was evaporated to give the product isopropyl purine (508 mg, 89%).

Preparation of 2-diethanolamino-6-(4-methoxybenzylamino)-9-isopropylpurine, (3).

The purine (1.65g, 4.98 mmol) was dissolved in DMSO (12 mL) and diethanolamine (4 mL) and then heated at 140° C. for 2–3 days and then at 160° C. for 1 day. The solution was cooled and water saturated butanol was added (100 mL). The solution was then washed with water (3×50 mL), before being evaporated to give a brown oil. The residue was chromatographed over silica gel eluting with ethyl acetate, followed by 3% methanol in ethyl acetate to give the product (730 mg, 37%) as a pale yellow oil.

Table 1 identifies compounds of this invention that were prepared according to the synthesis method set forth in this Example.

TABLE 1

Compounds Prepared by the Method of Example 1

| R₁X | R₂ | R₃ |
|---|---|---|
| (4-methoxyphenyl)methylamino | 3-cyanopropyl | Cl |
| (4-methoxyphenyl)methylamino | 3-chloropropyl | Cl |
| (4-methoxyphenyl)methylamino | benzyl | Cl |
| (4-methoxyphenyl)methylamino | (4-methylcarboxyphenyl)methyl | Cl |
| (4-methoxyphenyl)methylamino | 2-(N-phthaloyl)ethyl | Cl |
| (4-methoxyphenyl)methylamino | isopropyl | ethanolamino |
| (4-methoxyphenyl)methylamino | isopropyl | diethanolamine |
| (4-methoxyphenyl)methylamino | 3-methylbutyl | Cl |
| (4-methoxyphenyl)methylamino | 2-methylbutyl | Cl |
| (4-methoxyphenyl)methylamino | cyclopentyl | Cl |
| (4-methoxyphenyl)methylamino | (3-nitrophenyl)methyl | Cl |
| (4-methoxyphenyl)methylamino | (4-nitrophenyl)methyl | Cl |
| (4-methoxyphenyl)methylamino | ethyl | Cl |
| (4-methoxyphenyl)methylamino | propyl | Cl |
| (4-methoxyphenyl)methylamino | (3-methylphenyl)methyl | Cl |
| (4-methoxyphenyl)methylamino | (4-methylphenyl)methyl | Cl |
| heptylamino | H | Cl |
| N-benzyl-N-hydroxylamino | H | Cl |
| propylamino | H | Cl |
| noradamantylamino | H | Cl |
| cyclobutylamino | H | Cl |
| 3-methoxypropylamino | H | Cl |
| 2-methoxyethylamino | H | Cl |
| cyclopentylamino | H | Cl |
| 1-hydroxy-2-methyl-2-propylamino | H | Cl |
| (N-1-benzylpiperidinyl)-4-amino | H | Cl |
| heptylamino | Methyl | Cl |
| N-benzyl-N-hydroxylamino | Methyl | Cl |
| propylamino | Methyl | Cl |
| noradamantylamino | Methyl | Cl |
| cyclobutylamino | Methyl | Cl |
| 3-methoxypropylamino | Methyl | Cl |
| 2-methoxyethylamino | Methyl | Cl |
| cyclopentylamino | Methyl | Cl |
| 1-hydroxy-2-methyl-2-propylamino | Methyl | Cl |
| (N-1-benzylpiperidinyl)-4-amino | Methyl | Cl |
| (2,4-dimethoxyphenyl)methylamino | Methyl | Cl |
| (2-methoxyphenyl)methylamino | H | Cl |
| (2-pyridinyl)methylamino | H | Cl |
| (3,4-dimethoxyphenyl)ethylamino | H | Cl |
| (3-pyridinyl)methylamino | H | Cl |
| (4-pyridinyl)methylamino | H | Cl |
| 6-hydroxy-1-hexylamino | H | Cl |
| phenethylamino | H | Cl |
| (2-benzothiazolyl)amino | H | Cl |
| (2,4-dimethoxyphenyl)methylamino | H | Cl |
| (2-methoxyphenyl)methylamino | Methyl | Cl |
| (2-pyridinyl)methylamino | Methyl | Cl |
| (3,4-dimethoxyphenyl)ethylamino | Methyl | Cl |
| (4-methoxyphenyl)methylamino | Methyl | Cl |
| (3-pyridinyl)methylamino | isopropyl | 2-aminoethylamino |
| (4-pyridinyl)methylamino | H | Cl |
| 1-hydroxy-6-hexylamino | H | Cl |
| phenethylamino | H | Cl |
| (2-benzothiazolyl)amino | H | Cl |
| (4-methoxyphenyl)methylamino | H | Cl |
| 3-phenyl-1-propylamino | isopropyl | 3-hydroxypyrrolidino |
| (2-indanyl)amino | H | Cl |
| (4-methoxyphenyl)ethylamino | H | Cl |
| (4-nitrophenyl)methylamino | H | Cl |
| (2,6-difluorophenyl)methylamino | H | Cl |
| 3-phenyl-1-propylamino | H | Cl |
| (2-indanyl)amino | Methyl | Cl |
| (4-methoxyphenyl)ethylamino | Methyl | Cl |
| (4-nitrophenyl)methylamino | Methyl | Cl |
| (2,6-difluorophenyl)methylamino | Methyl | Cl |
| cyclopropylmethylamino | Methyl | Cl |
| 4-(1,2-methylenedioxyphenyl)methylamino | H | Cl |
| (4-aminosulfonylphenyl)methylamino | H | Cl |
| (cyclohexanol)-1-methylamino | H | Cl |
| (2-benzimidazolyl)methylamino | H | Cl |
| cyclohexylmethylamino | H | Cl |
| (4-methoxyphenyl)methylamino | H | Cl |

TABLE 1-continued

Compounds Prepared by the Method of Example 1

| R₁X | R₂ | R₃ |
|---|---|---|
| (4-methoxyphenyl)methylamino | isopropyl | (2-hydroxy-1-hydroxymethyl)ethylamino |
| cyclopropylmethylamino | isopropyl | 3-amino-2-hydroxypropylamino |
| 4-(1,2-methylene-dioxyphenyl)methylamino | Methyl | Cl |
| (4-aminosulfonyl-phenyl)methylamino | Methyl | Cl |
| (cyclohexanol)-1-methylamino | Methyl | Cl |
| (2-benzimidazolyl)methylamino | Methyl | Cl |
| cyclohexylmethylamino | Methyl | Cl |
| (3-pyridinyl)methylamino | Methyl | Cl |
| (4-pyridinyl)methylamino | 2-methylpropyl | Cl |
| 6-hydroxyhexylamino | cyclopentyl | Cl |
| phenethylamino | propyl | Cl |
| (2-benzothiazolyl)amino | ethyl | Cl |
| 3-phenyl-1-propylamino | isopropyl | Cl |
| (2-indanyl)amino | 2-methylpropyl | Cl |
| 2-(4-methoxyphenyl)ethylamino | cyclopentyl | Cl |
| (4-nitrophenyl)methylamino | propyl | Cl |
| (2,6-difluorophenyl)methylamino | ethyl | Cl |
| (4-methoxyphenyl)methylamino | isopropyl | Cl |
| 3-phenyl-1-propylamino | isopropyl | 4-hydroxypiperidino |
| (2-indanyl)amino | H | Cl |
| 2-(4-methoxyphenyl)ethylamino | H | Cl |
| (4-nitrophenyl)methylamino | H | Cl |
| (2,6-difluorophenyl)methylamino | H | Cl |
| (4-methoxyphenyl)methylamino | H | Cl |
| (4-methoxyphenyl)methylamino | isopropyl | N-(2-cyanoethyl)-N-benzylamino |
| 3-phenyl-1-propylamino | isopropyl | 1-(R,S)-hydroxymethyl-3-methylbutylamino |
| (2-indanyl)amino | isopropyl | Cl |
| 2-(4-methoxyphenyl)ethylamino | isopropyl | Cl |
| (4-nitrophenyl)methylamino | isopropyl | Cl |
| (2,6-difluorophenyl)methylamino | isopropyl | Cl |
| (4-methoxyphenyl)methylamino | isopropyl | Cl |
| (4-methoxyphenyl)methylamino | isopropyl | piperidino |
| (4-methoxyphenyl)methylamino | isopropyl | 3-hydroxypiperidino |
| 3-phenyl-1-propylamino | isopropyl | 1-(S)-hydroxymethyl-2-(4'-imidazolyl)ethylamino |
| (2-indanyl)amino | isopropyl | diethanolamino |
| (4-methoxyphenyl)methylamino | isopropyl | diethanolamino |
| (4-methoxyphenyl)methylamino | isopropyl | 2-(S)-hydroxymethylpyrrolidino |
| (4-methoxyphenyl)methylamino | isopropyl | diethanolamino |
| (4-methoxyphenyl)methylamino | benzyl | morpholino |
| (4-methoxyphenyl)methylamino | 3-methylbutyl | diethanolamino |
| (4-methoxyphenyl)methylamino | 2-methylbutyl | diethanolamino |
| (4-methoxyphenyl)methylamino | cyclopentyl | diethanolamino |
| (4-methoxyphenyl)methylamino | (3-nitrophenyl)methylamino | diethanolamino |
| (4-methoxyphenyl)methylamino | (4-nitrophenyl)methylamino | diethanolamino |
| (4-methoxyphenyl)methylamino | ethyl | diethanolamino |
| (4-methoxyphenyl)methylamino | propyl | diethanolamino |
| (4-methoxyphenyl)methylamino | (3-methylphenyl)methylamino | diethanolamino |
| heptylamino | (4-methylphenyl)methylamino | diethanolamino |
| N-benzyl-N-hydroxyamino | methyl | diethanolamino |
| propylamino | methyl | diethanolamino |
| noradamantylamino | methyl | diethanolamino |
| cyclobutylamino | methyl | diethanolamino |
| 3-methoxypropylamino | methyl | diethanolamino |
| 2-methoxyethylamino | methyl | diethanolamino |
| cyclopentylamino | methyl | diethanolamino |
| 1-hydroxy-2-methyl-2-propylamino | methyl | diethanolamino |
| 4-(1-benzylpiperidinyl)amino | methyl | diethanolamino |
| (4-methoxyphenyl)methylamino | methyl | diethanolamino |
| (4-methoxyphenyl)methylamino | isopropyl | diethanolamino |
| (2,4-dimethoxy-phenyl)methylamino | isopropyl | 3-hydroxypyrrolidino |
| (2-methoxyphenyl)methylamino | methyl | 2-(3'indolyl)ethylamino |
| (2-pyridinyl)methylamino | methyl | diethanolamino |
| 2-(3,4-dimethoxyphenyl)ethylamino | methyl | diethanolamino |
| (3-pyridinyl)methylamino | methyl | diethanolamino |
| (4-pyridinyl)methylamino | methyl | diethanolamino |
| 6-hydroxy-1-hexylamino | methyl | diethanolamino |

TABLE 1-continued

Compounds Prepared by the Method of Example 1

| R₁X | R₂ | R₃ |
|---|---|---|
| phenethylamino | methyl | diethanolamino |
| (2-benzothiazolyl)amino | methyl | diethanolamino |
| 3-phenyl-1-propylamino | methyl | diethanolamino |
| (2-indanyl)amino | methyl | diethanolamino |
| 2-(4-methoxyphenyl)ethylamino | methyl | diethanolamino |
| (4-nitrophenyl)methylamino | methyl | diethanolamino |
| (2,6-difluorophenyl)methylamino | methyl | diethanolamino |
| cyclopropylmethylamino | methyl | diethanolamino |
| 4-(1,2-methylenedioxy-phenyl)methylamino | methyl | diethanolamino |
| (4-aminosulfonylphenyl)-methylamino | methyl | diethanolamino |
| (cyclohexanol)-1-methylamino | methyl | diethanolamino |
| (2-benzimidazolyl)methylamino | methyl | diethanolamino |
| cyclohexylmethylamino | methyl | diethanolamino |
| (3-pyridyl)methylamino | methyl | diethanolamino |
| (4-pyridyl)methylamino | 2-methylpropyl | diethanolamino |
| 6-hydroxy-1-hexylamino | cyclopentyl | diethanolamino |
| 2-phenethylamino | propyl | diethanolamino |
| (2-benzothiazolyl)amino | ethyl | diethanolamino |
| 3-phenyl-1-propylamino | isopropyl | diethanolamino |
| (2-indanyl)amino | 2-methylpropyl | diethanolamino |
| 2-(4-methoxyphenyl)ethylamino | cyclopentyl | diethanolamino |
| (4-nitrophenyl)methylamino | propyl | diethanolamino |
| (2,6-difluorophenyl)methylamino | ethyl | diethanolamino |
| (4-methoxyphenyl)methylamino | isopropyl | diethanolamino |
| (4-methoxyphenyl)methylamino | isopropyl | 1-hydroxymethylcyclopentylamino |
| (4-methoxyphenyl)methylamino | isopropyl | 2-(R,S)-hydroxymethylpiperidino |
| cyclopropylmethylamino | isopropyl | 2,3-dihydroxy-1-propylamino |
| 4-(1,2-methylenedioxyphenyl)methylamino | isopropyl | Cl |
| (4-aminosulfonylphenyl)methylamino | isopropyl | Cl |
| (cyclohexanol)-1-methylamino | isopropyl | Cl |
| (2-benzimidazolyl)amino | isopropyl | Cl |
| cyclohexylmethylamino | isopropyl | Cl |
| 3-phenyl-1-propylamino | isopropyl | Cl |
| cyclopropylmethylamino | cyclopentyl | Cl |
| 4-(1,2-methylenedioxyphenyl)methylamino | isopropyl | diethanolamino |
| (4-methoxyphenyl)methylamino | isopropyl | diethanolamino |
| (4-methoxyphenyl)methylamino | isopropyl | diisopropylamino |
| (4-methoxyphenyl)methylamino | isopropyl | (trans-2-hydroxycyclohexyl)amino |
| (4-methoxyphenyl)methylamino | isopropyl | 2(R)-(1-hydroxy-3-phenyl)propylamino |
| (4-methoxyphenyl)methylamino | isopropyl | 5-(S)-(2,2-dimethyl-4(S)-phenyldioxalanyl)amino |

EXAMPLE 2

This Example describes a method for preparing compounds of this invention. The synthesis method disclosed in this Example is only slightly modified from that disclosed in Example 1.

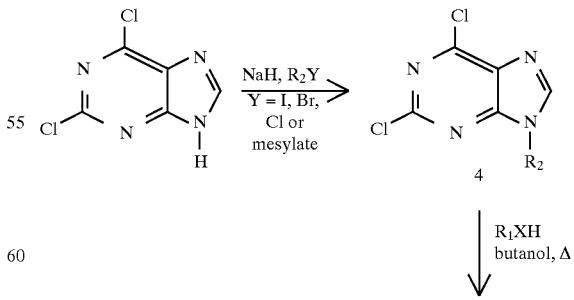

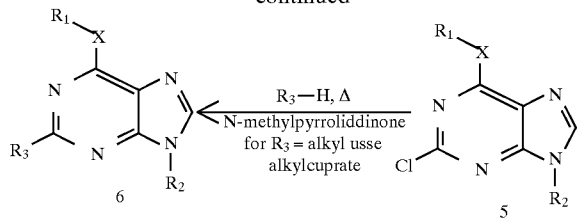

The following compound was prepared according to the method above.

Preparation of 2,6-dichloro-9-isopropylpurine (4).

To a solution of 0.67 g of 2,6-dichloropurine in 5 mL of dry DMF at room temperature was added 0.16 gms (1.1 eq.) of 50% sodium hydride/oil powder. Upon cessation of hydrogen evolution, a large excess (2 mL) of isopropyl iodide was added to the anionic solution. This reaction solution was stirred for three days at ambient temperature. The reaction was quenched with 30 mL of water and extracted with ethyl acetate (3×50 mL). The organic extracts were combined and back washed with 3×50 mL of water followed by 20 mL of brine. The ethyl acetate solution was dried over anhydrous magnesium sulfate and evaporated. The compound was subjected to variable gradient flash chromatography on silica gel with hexane/ethyl acetate mixtures and yielded 0.37 gms of desired N-9 product (45%) and 0.08 gms of the N-7 isomer(10%).

Preparation of 2-chloro-6-anilino-9-isopropylpurine (5).

2,6-dichloro-9-isopropylpurine (0.019 g, 0.081 mmol) was dissolved in butanol (0.5 ml) and aniline (0.044 ml, 0.244 mmol) was added. The reaction mixture was heated to 120° C. for 10 hr, cooled, diluted with EtOAc and washed 3 times with water. The mixture was dried over MgSO$_4$ and concentrated to an off white solid.

Preparation of 2-diethanolamino-6-(4-phenylanilino)-9-isopropylpurine (6).

A solution of 67 mgs of 2,6-dichloro-N-9-isopropylpurine and 100 mgs of 4-phenylaniline in 1 mL of n-octanol was heated to 80° C. for 24 hours. The n-octanol was removed in vacuo and then replaced with 1 mL of 40% diethanolamine in DMSO. The solution was heated at 130° C. for 48 hours. The reaction was cooled to ambient temperature then diluted with 10 mL of water and subsequently extracted with ethyl acetate (3×30 mL). The organic extracts were combined and back washed with 3×20 mL of water followed by 10 mL of brine. The ethyl acetate solution was dried over anhydrous magnesium sulfate and filtered and the solvent was evaporated. The 65 mgs of crude product was crystallized from THF-ether solution to yield 28mgs of pure product(23%).

Table 2 below identifies compounds of this invention that were prepared according to the general synthesis method set forth in this Example.

TABLE 2

Compounds Prepared According to the Method of Example 2

| R$_1$X | R$_2$ | R$_3$ |
|---|---|---|
| (8-quinolinyl)amino | isopropyl | Cl |
| (6-quinolinyl)amino | isopropyl | Cl |
| (3-quinolinyl)amino | isopropyl | Cl |
| anilino | isopropyl | Cl |
| 3,5-dinitroanilino | isopropyl | Cl |
| 4-butylanilino | isopropyl | Cl |
| (8-quinolinyl)amino | isopropyl | diethanolamino |
| (6-quinolinyl)amino | isopropyl | diethanolamino |
| (3-quinolinyl)amino | isopropyl | diethanolamino |
| anilino | isopropyl | diethanolamino |
| 3,5-dinitroanilino | isopropyl | diethanolamino |
| 4-butylanilino | isopropyl | diethanolamino |
| (6-ethoxy-2-benzothiazolyl)amino | isopropyl | Cl |
| 4-morpholino-2-methylamino | isopropyl | Cl |
| (4-aminosulfonyl-phenyl)methylamino | isopropyl | Cl |
| 4-bromoanilino | isopropyl | diethanolamino |
| 3,4-dichloroanilino | isopropyl | diethanolamino |
| 2-(2-(1-methyl)pyrrolidinyl)ethylamino | isopropyl | diethanolamino |
| 3-bromoanilino | isopropyl | Cl |
| 4-methoxyanilino | isopropyl | diethanolamino |
| 4-iodoanilino | isopropyl | Cl |
| 3-iodoanilino | isopropyl | Cl |
| 3-methoxyanilino | isopropyl | Cl |
| 2-(1-piperidinyl)ethylamino | isopropyl | diethanolamino |
| 2-(1-pyrrolidinyl)ethylamino | isopropyl | diethanolamino |
| (1-indanyl)amino | isopropyl | diethanolamino |
| 2-(6-ethoxybenzothiazolyl)amino | isopropyl | diethanolamino |
| 4-morpholino-2-methylamino | isopropyl | diethanolamino |
| (4-aminosulfonyl-phenyl)methylamino | isopropyl | diethanolamino |
| 4-bromoanilino | isopropyl | diethanolamino |
| 3,4-dichloroanilino | isopropyl | diethanolamino |
| 2-(2-(1-methyl)pyrrolidinyl)ethylamino | isopropyl | diethanolamino |
| 3-bromoanilino | isopropyl | diethanolamino |
| 4-methoxyanilino | isopropyl | diethanolamino |
| 4-iodoanilino | isopropyl | diethanolamino |
| 3-iodoanilino | isopropyl | diethanolamino |
| 3-methoxyanilino | isopropyl | diethanolamino |
| 2-(1-piperidinyl)ethylamino | isopropyl | diethanolamino |
| 2-(1-pyrrolidinyl)ethylamino | isopropyl | diethanolamino |
| (1-indanyl)amino | isopropyl | diethanolamino |
| 3-iodoanilino | isopropyl | diethanolamino |
| 3-phenoxyanilino | isopropyl | diethanolamino |
| 4-iodoanilino | isopropyl | diethanolamino |
| 4-phenoxyanilino | isopropyl | diethanolamino |
| 3-phenoxyanilino | isopropyl | diethanolamino |
| 2-fluorenylamino | isopropyl | diethanolamino |
| 1-fluorenylamino | isopropyl | diethanolamino |
| 2-anthracenylamino | isopropyl | diethanolamino |
| 1-anthracenylamino | isopropyl | diethanolamino |
| 2-(6-ethoxybenzothiazolyl)amino | isopropyl | diethanolamino |
| (1-indanyl)amino | isopropyl | diethanolamino |
| 2-(6-ethoxybenzothiazolyl)amino | isopropyl | diethanolamino |
| 4-morpholino-2-methylamino | isopropyl | diethanolamino |
| (4-aminosulfonyl-phenyl)methylamino | isopropyl | diethanolamino |
| 4-bromoanilino | isopropyl | diethanolamino |
| 3,4-dichloroanilino | isopropyl | diethanolamino |
| 2-(2-(1-methyl)pyrrolidinyl)ethylamino | isopropyl | diethanolamino |
| 3-bromoanilino | isopropyl | diethanolamino |
| 4-methoxyanilino | isopropyl | diethanolamino |
| 4-iodoanilino | isopropyl | diethanolamino |
| 3-iodoanilino | isopropyl | diethanolamino |
| 3-methoxyanilino | isopropyl | diethanolamino |
| 2-(1-piperidinyl)ethylamino | isopropyl | diethanolamino |
| 2-(1-pyrrolidinyl)ethylamino | isopropyl | diethanolamino |
| (1-indanyl)amino | isopropyl | diethanolamino |
| 3-iodoanilino | isopropyl | diethanolamino |
| 3-phenoxyanilino | isopropyl | diethanolamino |
| 4-iodoanilino | isopropyl | diethanolamino |
| 4-phenoxyanilino | isopropyl | diethanolamino |
| 3-phenoxyanilino | isopropyl | diethanolamino |
| 2-fluorenylamino | isopropyl | diethanolamino |
| 1-fluorenylamino | isopropyl | diethanolamino |

TABLE 2-continued

Compounds Prepared According to the Method of Example 2

| $R_1X$ | $R_2$ | $R_3$ |
|---|---|---|
| 2-anthracenylamino | isopropyl | diethanolamino |
| 1-anthracenylamino | isopropyl | diethanolamino |
| 2-(6-ethoxybenzothiazolyl)amino | isopropyl | diethanolamino |
| (2-biphenyl)methylamino | isopropyl | diethanolamino |
| (4-biphenyl)methylamino | isopropyl | diethanolamino |
| 2-naphthylmethylamino | isopropyl | diethanolamino |
| 1-naphthylmethylamino | isopropyl | diethanolamino |

The description above has been offered for illustrative purposes only, and it is not intended to limit the scope of the invention of this application which is defined in the following claims.

EXAMPLE 3

CDK2 assays:

Compositions of this invention were assayed to determine their CDK2 inhibitory activity. The assay system (total volume of 50 µl) contained 50 mM Tris-Cl, pH 7.4, 10 mM $MgCl_2$, 5 mM DTT, 1µg of histone H1, 30 µM ATP (I µCi of gamma $32^P$ labeled ATP), 10 µg of BSA and 1 ng of purified CDK2. After incubation at 30° C. for 30 min, the reaction was terminated by the addition of 10 µl of 10% TCA and the samples were blotted onto to nitrocellulose filters. These filters were washed extensively in 10% TCA and assayed for radioactivity. Blanks contained no enzyme. To ascertain the potency of various compounds of this invention, the compounds were added to the above assay at concentrations ranging from 100 to 0.02 µg/mi. After incubation at 30 min., the assay tubes were processed as above. In all assays, various concentrations of olomoucine was added and was used as a standard positive control. The $IC_{50}$ (enzyme) listed in Table 3 is defined as the concentration required to inhibit CDK2 activity by 50%.

EXAMPLE 4

Cell Proliferation Assays:

Early passage rat aortic smooth muscle cells (CV Therapeutics Cell repository) were seeded in 48 well dishes (Falcon, ml/well) at a density of 20,000 cells/ml of DME containing 5% heat inactivated bovine serum. The cells were incubated in a standard tissue culture incubator for 48 hr. The medium was aspirated and the wells were replenished with 0.2 ml of fresh medium. Compounds of this invention were added at concentrations ranging from 100 to 0.37 µg/ml. After 48 hr incubation, the medium was aspirated and the cultures were treated with 0.2 ml of saline 0.25 µl of phenozine methosulfate solution containing MTS (Cell Titer® Aqueous Non-radioactive cell proliferation assay kit, Catalog # G 5430, Promega, 2800 Woods Hollow Road, Madison, Wis. 53711-5399). The $IC_{50}$ cells listed in Table 3 is defined as the concentration required to inhibit cell proliferation by 50%. Olomoucine at various concentrations was added and was used as a standard positive control.

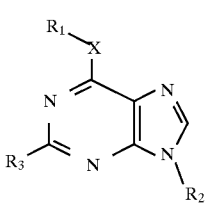

The inhibition of cell proliferation properties of the compounds of this invention are demonstrated by their ability to inhibit cell proliferation in the range of about 0.05 µg/ml to 100 µg/ml, preferably less than 0.5 µg/ml.

EXAMPLE 5

A compound of this invention was evaluated for effectiveness using the Murine Leukemia Model. The Murine Leukemia Model is a standard model used in the evaluation of antitumor agents. CDF1 mice were injected ip with L1210 cells ($1 \times 10^3$ cells/mouse). Twenty-four hours later, these mice were treated with various doses (ip) of compound 3 of Example 1 in saline. The dosing regimen used in this study is outlined in Table 4, below. Mice were dosed with compound 3 daily or on alternate days. Control mice received saline. After 7 days, dosing was suspended and survival monitored.

TABLE 4

| Treatment | | N | Median survival time Days | T/C × 100 |
|---|---|---|---|---|
| Saline control | | 7 | 10 (9–13) | 100 |
| Compound 3 | 0.5 mg/kg bid | 7 | 11 (10–15) | 110 |
| | 1.0 mg/kg bid | 7 | 13 (11–13) | 130 |
| | 2 mg/kg bid | 7 | 12 (10–14) | 120 |
| | 4 mg/kg — days 1,3,5,7 | 7 | 13 (10–15) | 130 |
| | 8 mg/kg — days 1,3,5,7 | 7 | 13 (12–16) | 130 |

The results indicate that rats administered compound 3 survived longer than the control rats.

EXAMPLE 6

This example measured the effect of an acute local delivery of compound 3 of Example 1 in reducing neointima formation following balloon angioplasty in the rat carotid artery model. In this example, the left common carotid arteries of adult male rats (n=10 per experimental group) were surgically injured using a Fogarty arterial embolectomy catheter. Immediately after injury, the common carotid artery was bisected with a vascular clamp, thereby establishing an untreated and treated segment. A drug delivery catheter was then inserted into the distal half of the common carotid. After drug delivery, the catheter was removed and excess drug was washed out by removing the vascular clamp and re-establishing blood flow before closing the artery. The animals were allowed to recover for 14 days before harvesting the common carotid artery. The harvested tissue was sectioned and the neointimal area was digitized and measured with a computer planimetery system. For each animal, 15 measurements were averaged for the untreated segment and 15 for the treated.

The results of this Example are found in FIG. 1. According to FIG. 1, administering compound 3 of Example 1 to a damaged carotid artery reduced the neointimal area about 88% in comparison to the 6% reduction produced by the saline vehicle alone.

What we claim is:

1. A 2,6,9-trisubstituted purine composition and salts thereof, the composition having the following formula:

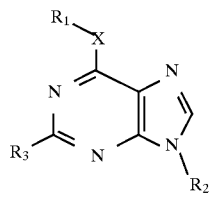 (I)

wherein

X is a —NH;

R$_1$ is selected from an aromatic carbocyclic group having one aromatic ring, and an aromatic carbocyclic group having one aromatic ring that is substituted with at least one substituent selected from halogen, lower alkyl, lower alkoxy, alkylthio, amino, carboxyl, hydroxyl, nitro, phenyl, cyano, —SH—C≡C—H, and —C(O)NRR' where R and R' are independently selected from hydrogen, lower alkyl, aryl, and hetaryl;

R$_2$ is selected from the group consisting of lower alkyl; and

R$_3$ is —NR$_4$R$_5$ wherein R$_4$ and R$_5$ are each —CH$_2$CH$_2$OH, —CHR'CH$_2$OH, or —CH$_2$CHR'OH wherein R' is hydrogen or alkyl having from 1 to 6 carbon atoms.

2. A 2,6,9-trisubstituted purine composition and salts thereof, the composition having the following formula:

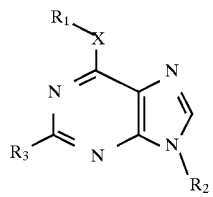 (I)

wherein;

X is a —NH;

R$_1$ is benzyl substituted with halogen, alkoxy, or nitro groups;

R$_2$ is selected from the group consisting of lower alkyl; and

R$_3$ is —NR$_4$R$_5$ wherein R$_4$ and R$_5$ are each —CH$_2$CH$_2$OH, —CHR'CH$_2$OH, or —CH$_2$CHR'OH wherein R' is hydrogen or alkyl having from 1 to 6 carbon atoms.

3. The 2,6,9-trisubstituted purine composition of claim 2 wherein RI is selected from 4-methoxybenzyl, 4-chlorobenzyl, and 4-nitro benzyl.

4. The 2,6,9-trisubstituted purine composition of claim 2 wherein R$_2$ is isopropyl.

5. The 2,6,9-trisubstituted purine composition of claim 2 wherein R$_4$ and R$_5$ are each —CH$_2$CH$_2$OH.

6. A 2,6,9-trisubstituted purine composition and salts thereof, the composition having the following formula:

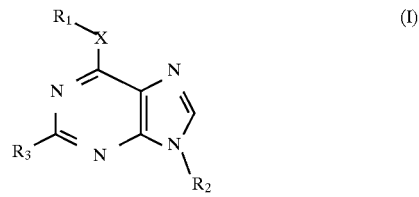 (I)

wherein

X is a —NH;

R$_1$ is biphenylmethyl;

R$_2$ is isopropyl; and

R$_3$ is —NR$_4$R$_5$ wherein R$_4$ and R$_5$ are each —CH$_2$CH$_2$OH.

* * * * *

UNITED STATES PATENT AND TRADEMARK OFFICE
CERTIFICATE OF CORRECTION

PATENT NO. : 5,866,702
DATED : February 2, 1999
INVENTOR(S) : Mackman, et al.

It is certified that error appears in the above-identified patent and that said Letters Patent is hereby corrected as shown below:

At column 2, line 56, insert -- -RHN, -- before "3-methyl-2-butenylamino" and after "not".

At column 3, line 27, delete 'DESCRIPTION" and replace with -- DESCRIPTION --.

At columns 13 and 14 insert the following entries omitted from the end of Table 1 and before "Example 2"

| (4-methoxyphenyl)methylamino | isopropyl | 3-(N-1-imidazolyl)propylamino |
|---|---|---|
| (4-methoxyphenyl)methylamino | isopropyl | 4-hydroxyl-4-phenylpiperidino |
| (4-methoxyphenyl)methylamino | isopropyl | (2-benzylthio-1-hydroxymethyl)ethylamino |
| (4-methoxyphenyl)methylamino | isopropyl | N-methyl-N-(2-hydroxy-2-(3,4-dihydroxyphenyl)ethyl)amino |
| (4-methoxyphenyl)methylamino | isopropyl | diallylamino |
| (4-methoxyphenyl)methylamino | isopropyl | Piperazino |
| (4-methoxyphenyl)methylamino | isopropyl | (+/-)N-methyl-N-(2-hydroxy-2-phenylethyl)amino |
| (4-methoxyphenyl)methylamino | isopropyl | (S)-(+)-2-(anilinomethyl)pyrrolidino |
| (4-methoxyphenyl)methylamino | isopropyl | (+/-)N-(2-propenyl)-N-2-(4-hydroxy-2-methylpentyl)amino |

UNITED STATES PATENT AND TRADEMARK OFFICE
CERTIFICATE OF CORRECTION

PATENT NO. : 5,866,702
DATED : February 2, 1999
INVENTOR(S) : Mackman, et al.

It is certified that error appears in the above-identified patent and that said Letters Patent are hereby corrected as shown below:

| | | |
|---|---|---|
| (4-methoxyphenyl)methylamino | isopropyl | N-(2-hydroxyethyl)-N-(3-hydroxypropyl)amino |
| (4-methoxyphenyl)methylamino | isopropyl | Di-N-1-(2-hydroxy-2-methylpentyl)amino |
| (4-methoxyphenyl)methylamino | isopropyl | Di-N-2-(3-hydroxybutyl)amino |

At column 17, line 30, delete "$32^P$" and replace with -- $32_p$ --.

At column 17, line 62, delete "Titer®" and replace with --Titer 96® --.

At column 18, line 9, insert the following Table 3

UNITED STATES PATENT AND TRADEMARK OFFICE
CERTIFICATE OF CORRECTION

PATENT NO. : 5,866,702
DATED : February 2, 1999
INVENTOR(S) : Mackman, et al.

It is certified that error appears in the above-identified patent and that said Letters Patent are hereby corrected as shown below:

Table 3

Bioactivity of Selected Representatives of this Invention

| $R_1$-X | $R_2$ | $R_3$ | $IC_{50}(\mu g/mL)$ enzyme | $IC_{50}(\mu g/mL)$ cells |
|---|---|---|---|---|
| benzylamino | Me | ethanolamino | 7 | 70 |
| 4-methoxybenzylamino | H | Cl | 60 | NA |
| 4-methoxybenzylamino | Me | Cl | 6 | Inactive |
| 4-methoxybenzylamino | Me | ethanolamino | 4 | 48 |
| 4-chlorobenzyloxy | H | Cl | 60 | NA |
| 4-chlorobenzyloxy | Me | Cl | 60 | NA |
| 4-chlorobenzyloxy | trifluoromethyl | Cl | >60 | NA |
| 4-methoxybenzylamino | isopropyl | Cl | 4 | 77 |
| 4-methoxybenzylamino | isopropyl | ethanolamino | 4 | 43 |
| 4-methoxybenzylamino | Me | diethanolamino | 4 | 48 |
| 4-methoxybenzylamino | 2-methylpropyl | Cl | 60 | >70 |
| ethanolamino | Me | ethanolamino | >60 | >70 |
| 4-methoxybenzylamino | trifluoromethyl | Cl | >60 | >70 |
| 4-methoxybenzylamino | benzyl | Cl | >60 | >70 |

UNITED STATES PATENT AND TRADEMARK OFFICE
CERTIFICATE OF CORRECTION

PATENT NO. : 5,866,702　　　　　　　　　　Page 4 of 5
DATED : February 2, 1999
INVENTOR(S) : Mackman, et al.

It is certified that error appears in the above-identified patent and that said Letters Patent are hereby corrected as shown below:

| $R_1$-X | $R_2$ | $R_3$ | $IC_{50}(\mu g/mL)$ enzyme | $IC_{50}(\mu g/mL)$ cells |
|---|---|---|---|---|
| ethanolamino | H | benzylamino | >60 | NA |
| 4-methoxybenzylamino | isopropyl | diethanolamino | 0.2 | 2.1 |
| 4-methoxybenzylamino | perfluoroisopropyl | Cl | >45 | NA |
| 4-methoxybenzylamino | perfluoroisopropyl | diethanolamino | 40 | NA |
| 4-methoxybenzylamino | ispropyl | 3-hydroxy-pyrrolidino | 1 | 12.5 |
| 4-methoxybenzylamino | hydroxyethyl | diethanolamino | 0.5 | 62 |
| 4-methoxybenzylamino | isopropyl | 2-hydroxy-1-hydroxymethylethylamino | 0.4 | 15 |
| 4-methoxybenzylamino | isopropyl | 3-amino-2-hydroxypropylamino | 0.6 | 25 |
| 4-methoxybenzylamino | 3-cyanopropyl | Cl | >60 | NA |
| 4-methoxybenzylamino | 3-chloropropyl | Cl | >60 | NA |
| 4-methoxybenzylamino | benzyl | Cl | >60 | NA |

UNITED STATES PATENT AND TRADEMARK OFFICE
CERTIFICATE OF CORRECTION

PATENT NO. : 5,866,702
DATED : February 2, 1999
INVENTOR(S) : Mackman, et al.

It is certified that error appears in the above-identified patent and that said Letters Patent are hereby corrected as shown below:

| $R_1$-X | $R_2$ | $R_3$ | $IC_{50}(\mu g/mL)$ enzyme | $IC_{50}(\mu g/mL)$ cells |
|---|---|---|---|---|
| 4-methoxybenzylamino | (4-methylcarboxyphenyl)methyl | Cl | >60 | NA |
| 4-methoxybenzylamino | 2-(N-Phthaloyl)ethyl | Cl | >60 | NA |

At column 20, line 14, delete "RI" and replace with -- $R_1$ --.

Signed and Sealed this

Third Day of August, 1999

Attest:

Attesting Officer

Q. TODD DICKINSON

Acting Commissioner of Patents and Trademarks